United States Patent [19]

Davidson

[11] Patent Number: 5,540,898

[45] Date of Patent: Jul. 30, 1996

[54] OZONE GENERATOR WITH IN-LINE OZONE SENSOR

[75] Inventor: William E. Davidson, Scarborough, Canada

[73] Assignee: Vasogen Inc., Etobicoke, Canada

[21] Appl. No.: 489,568

[22] Filed: Jun. 12, 1995

Related U.S. Application Data

[63] Continuation of PCT/CA95/00315, May 26, 1995.

[30]    Foreign Application Priority Data

May 26, 1995 [WO]  WIPO ................... PCT/CA95/00315

[51] Int. Cl.$^6$ ........................................... B01J 19/08
[52] U.S. Cl. ........................... 422/186.15; 422/186.16; 422/186.29
[58] Field of Search ................... 422/186.15, 186.16, 422/186.29

[56]            References Cited

U.S. PATENT DOCUMENTS

| | | | |
|---|---|---|---|
| 3,169,524 | 2/1965 | Langevin | 128/172.1 |
| 3,838,290 | 9/1974 | Crooks | 250/532 |
| 4,307,433 | 12/1981 | Takechi et al. | 361/231 |
| 4,632,980 | 12/1986 | Zee et al. | 530/380 |
| 4,877,588 | 10/1989 | Ditzler et al. | 422/186.19 |
| 4,966,666 | 10/1990 | Waltonen | 204/164 |
| 5,052,382 | 10/1991 | Wainwright | 128/202.25 |
| 5,091,069 | 2/1992 | Hendrickson et al. | 204/176 |
| 5,135,725 | 8/1992 | Hendrickson et al. | 422/186.15 |
| 5,145,350 | 9/1992 | Dawson et al. | 422/186.15 |
| 5,268,151 | 12/1993 | Reed et al. | 422/186.16 |
| 5,278,492 | 1/1994 | Huynh et al. | 323/326 |
| 5,285,372 | 2/1994 | Huynh et al. | 363/132 |
| 5,359,997 | 11/1994 | Rigo et al. | 128/202.16 |
| 5,411,713 | 5/1995 | Iwanaga | 422/186.15 |
| 5,443,800 | 8/1995 | Dunder | 422/186.16 |
| 5,474,750 | 12/1995 | Racca et al. | 422/186.15 |

FOREIGN PATENT DOCUMENTS

| | | | |
|---|---|---|---|
| 1324340 | 11/1993 | Canada | B01J 19/08 |
| 0339924A2 | 4/1989 | European Pat. Off. . | |
| 4270102 | 2/1991 | Japan . | |
| 5201704 | 1/1992 | Japan . | |
| 7041305 | 7/1993 | Japan . | |
| 2195189 | 9/1986 | United Kingdom . | |
| WO89/11908 | 5/1989 | WIPO . | |

Primary Examiner—Donald P. Walsh
Assistant Examiner—Daniel Jenkins
Attorney, Agent, or Firm—Ridout & Maybee

[57]             ABSTRACT

An apparatus for generating ozone from an oxygen supply. The apparatus comprises electrodes mounted in an enclosure and a high voltage circuit coupled to the electrodes for generating an electric field. The high voltage circuit receives AC power and includes a control circuit for producing a linearly controlled high voltage output from the AC feed for energizing the electrodes. The apparatus also includes an in-line sensor for determining the level of ozone being produced without affecting the ozone concentration. The high voltage circuit is also suitable for other applications where a precisely controlled high voltage output signal is needed.

19 Claims, 2 Drawing Sheets

5,540,898

OZONE GENERATOR WITH IN-LINE OZONE SENSOR

This application is a continuation of my application in a PCT/CA95/00315 application filed May 26, 1995.

FIELD OF THE INVENTION

This invention relates to apparatus for generating ozone gas, and more particularly to an apparatus with an in-line sensor which is suitable for applications in which the concentration of ozone gas needs to be carefully controlled.

BACKGROUND OF THE INVENTION AND PRIOR ART

In the art, ozone generators are well known. U.S. Pat. No. 5,052,382, which issued to Wainwright on Oct. 1, 1991, described an apparatus for the controlled generation and administration of ozone gas. The apparatus disclosed by Wainwright comprises a generator for generating the ozone, a monitor for monitoring the ozone, a dosage device for providing the amount of ozone and a computer for controlling operation of the apparatus.

While Wainwright discloses an ozone generating apparatus suitable for medical application, there are aspects which affect the performance and accuracy of the device. The monitor or sensor taught by Wainwright comprises an ultra violet light source and a strobed detector. The detector is strobed by a zeon light source, but according to Wainwright, it may be strobed by another light source. As will be understood by those skilled in the art, this arrangement comprises an intrusive measurement technique. According to this technique, the ozone and oxygen gas stream is exposed to ultra violet light. The UV light interacts with the ozone and the amount of UV light which is measured by the sensor will be dependent on the concentration of the ozone gas. Because there is an interaction between the UV light and the ozone gas, the UV light affects the concentration of the ozone gas which is produced by the generator. Therefore, the ozone generator taught by Wainwright is not well-suited for applications where the ozone concentration must be very accurately controlled, nor is the Wainwright device suited for an application where the ozone sensor is in-line with the treatment.

It is object of the present invention to provide an apparatus for generating ozone gas having an electronic circuit capable of carefully controlling the amount of ozone being generated. It is another object of the present invention to provide an apparatus for generating ozone gas having a non-intrusive sensor for sensing the concentration of the ozone gas being produced. It is another object of the present invention to provide an ozone sensor which can be located "in-line" with the treatment path.

SUMMARY OF THE INVENTION

According to one aspect of the present invention, there is provided an apparatus for generating ozone from an oxygen supply, said apparatus comprising: (a) an enclosure having an inlet for receiving said oxygen supply and an outlet for releasing said ozone and said oxygen; (b) a plurality of electrodes mounted inside said enclosure and said electrodes being separated by a dielectride, (c) energizer means for energizing said electrodes, said energizer means having a control input for receiving a control signal and an input port for connecting to a power source, and (d) said energizer means including generator means responsive to said control signal for generating a high voltage at an output coupled to said electrodes for energizing said electrodes and producing an electric field for forming ozone from said oxygen.

According to another aspect of the present invention, there is provided a bridge network and control circuit for linearly controlling the AC signal. The apparatus for linearly controlling an AC signal comprising (a) a bridge network having an input port for receiving an AC signal, and said bridge network including a switching control input and a bridge output port; (b) a control circuit having an input for receiving a control signal and an output coupled to the switching control input of said bridge network, and said control circuit having means for generating a switching control signal at said output for switching said bridge network and producing a controlled power signal at said bridge output port; and (c) a transformer having an output port and an input port coupled to said bridge output port and means responsive to said controlled power signal for producing a high voltage output signal at said output port.

BRIEF DESCRIPTION OF THE DRAWINGS

Reference will now be made to the drawing which illustrates, by way of example, a preferred embodiment of the present invention.

DETAILED DESCRIPTION OF THE PREFERRED EMBODIMENTS

Figure 1:
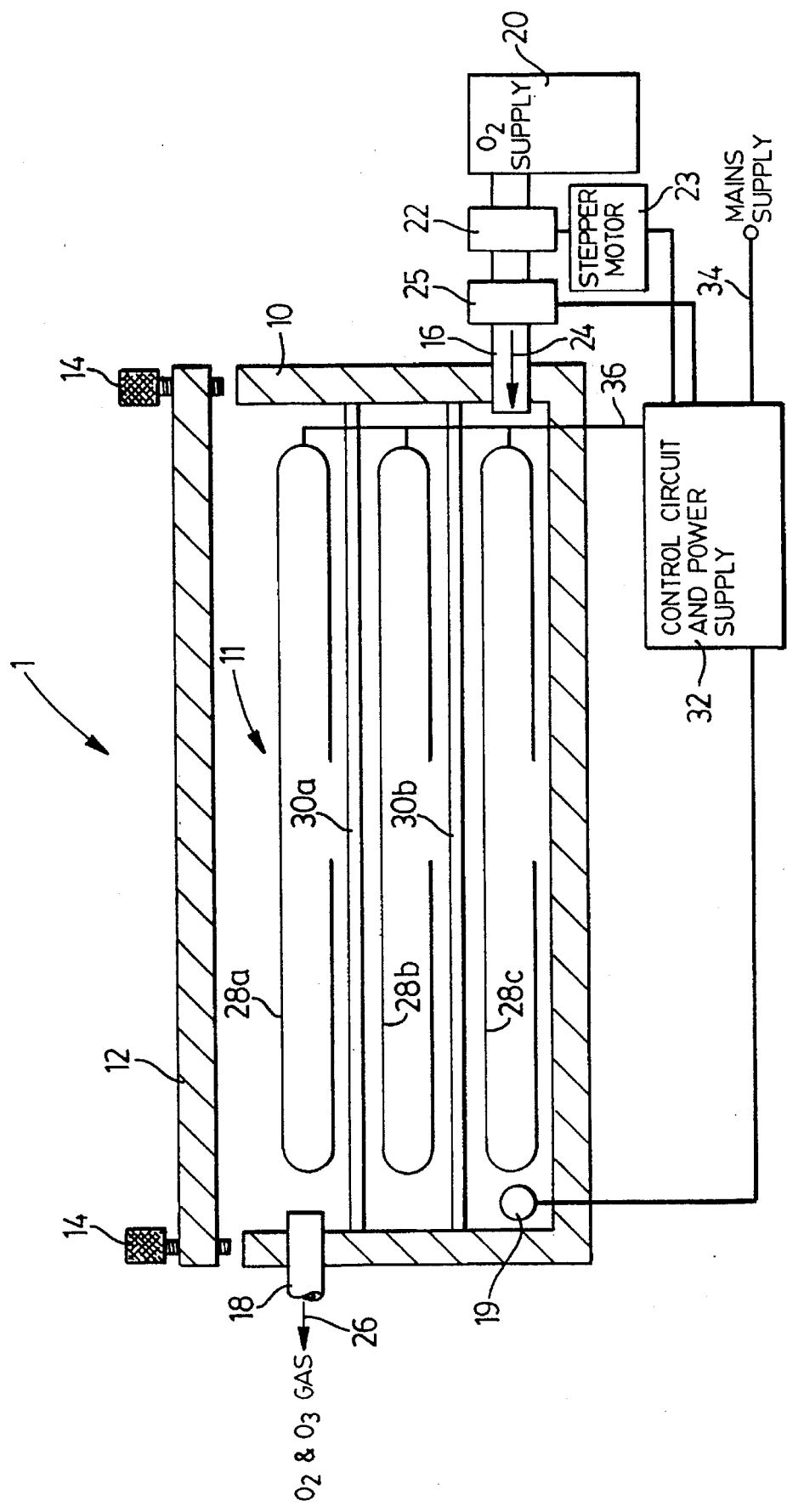
FIG. 1 is a diagrammatic illustration of an apparatus according to a specific embodiment of the present invention.

Reference is first made to FIG. 1 which shows an ozone generator 1 according to the present invention. The ozone generator 1 is suitable for the generation of carefully measured amounts of ozone gas and has particular though by no means exclusive application to medical applications. The apparatus and particularly the control circuit have wider applicability, such as applications outside of ozone generators where high voltage needs to be carefully controlled.

As shown in FIG. 1, the ozone generator 1 comprises a housing or enclosure 10. The housing 10 is formed from PTFE material commonly known as Teflon™, preferably medical grade. Teflon is preferred because it is an inert substance which is impervious to ozone and preferably the housing 10 is milled from a solid block of Teflon™. The housing 10 can also be made from Kynar™ material available from the Pennwalt Corporation and other compositions such as CPCVC or silicon which are of medical grade. As shown, the housing 10 includes a lid 12 which is also made from medical grade Teflon™. The lid 12 is attached to the enclosure 10 by secure fasteners 14, for example, precision screws. The enclosure 10 includes an inlet port 16 and an outlet port 18. The inlet 16 provides the input for oxygen gas 24 and is coupled to an oxygen supply tank 20 through a gas flow control valve 22. The gas flow control valve 22 is coupled to control circuit 32 through a stepper motor 23 or other appropriate actuator. A flow meter 25 is also included which provides the rate of flow of the oxygen gas 24 into the enclosure 10. The outlet port 18 provides an output for gas 26 comprising oxygen and ozone produced by the generator 1. As shown in FIG. 1, a temperature sensor 19 can also be provided to sense the temperature inside the enclosure 10. The control circuit 32 uses the temperature readings to control the production of ozone.

The ozone generator 1 includes a series of grids or 28a, 28b, 28c or other suitable electrodes which are mounted in a spaced relationship inside the chamber 11 formed by the enclosure 10 as shown in FIG. 1. Preferably, the grids 28a, 28b, 28c are made from high-grade stainless steel. A pair of mica sheets 30a,30b separate the grids 28. Other suitable dielectrics, such as glass, can be used to separate the grids 28. The ozone generator 1 has a control circuit and power supply module 32. The control circuit 32 is powered by conventional AC power 34, i.e. main supply. The control circuit 32 has a high voltage output 36 which connects to the grids 28a,28b,28c. The control circuit 32 biases the grids 28a, 28b,28c to a high voltage level to produce an electric field which causes the formation of ozone gas $O_2$ in the stream of oxygen 24 which enters the chamber 11 through the inlet port 16 and passes over the electrodes 28. The circuit 32 uses the gas flow control valve 22 to regulate the amount of oxygen 24 entering the chamber 11. The ozone generator 1 can also include a relay 33 (FIG. 2) as a safety feature which is activated by the control circuit 32 to enable the high voltage feed to the electrodes 28.

Figure 2:
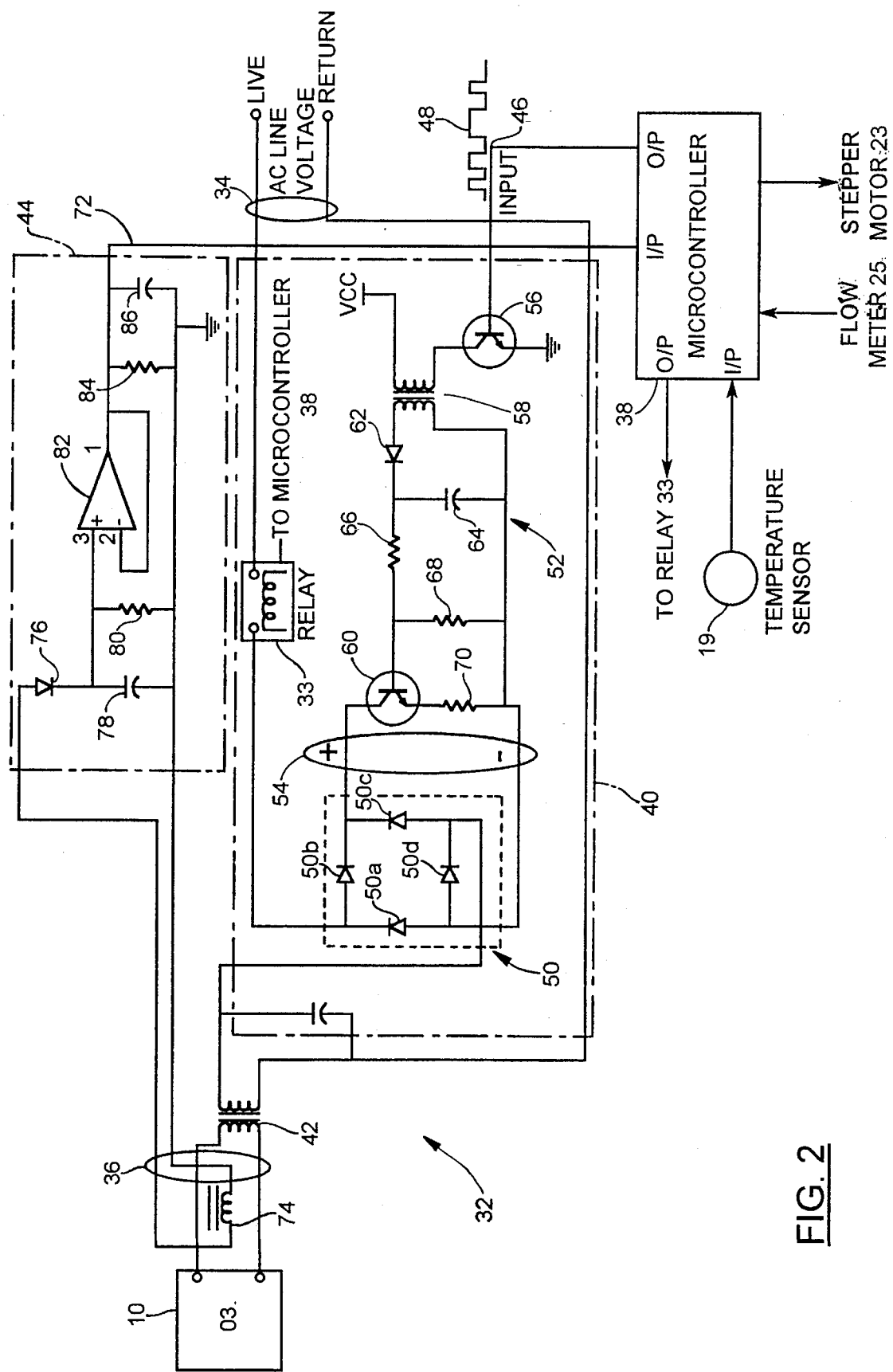
FIG. 2 is a schematic diagram of the control circuitry for the embodiment shown in FIG. 1.

Reference is next made to FIG. 2, which shows the control circuit 32 in more detail. The control circuit 32 preferably comprises a microprocessor based circuit suitably programmed for operating the gas flow control valve 22 and the ozonizer 1.

As shown in FIG. 2, the control circuit 32 comprises a microcontroller 38, a high voltage drive circuit 40, a high voltage transformer 42, and a sensing circuit 44. The high voltage drive circuit 40 is connected to the transformer 42 which produces the high voltage output for biasing the grids 28. The sensing circuit 44 is coupled to the output of the transformer 42 and is used by the microcontroller 38 to determine the amount of zone gas $O_2$ being generated as will be described below.

The high voltage drive 40 has an input 46 connected to an output port of the microcontroller 38 for receiving a control signal 48. The control signal 48 comprises a pulse train which is generated by the microcontroller 38. The high-voltage drive circuit 40 as shown in FIG. 2 comprises a bridge network 50 and a bridge control circuit 52. The bridge network 50 comprises four diodes 50a,50b,50c,50d connected in a bridge configuration. As shown in FIG. 2, the bridge network 50 couples the "live" AC voltage 34 to the primary winding of the high voltage transformer 42. The current flowing in the primary winding or the transformer 42 is controlled by the circuit 52 which is coupled to the other port 54 of the bridge 50. The current which flows in the bridge 50 and primary winding induces a voltage in the secondary winding of the high voltage transformer 42 which biases the grids 28 (FIG. 1).

The function of the bridge network 50 and the bridge control circuit 52 is to regulate the current flowing in the primary winding and thereby the high voltage induced in the secondary winding of the transformer 42 and applied to the grids 28. By regulating the high voltage applied to the grids 28, the amount of ozone gas $O_3$ which is generated can be carefully controlled. As will be described, the bridge control circuit 52 together with the control signal 48 regulate both the shape and level of the high voltage signal which biases the grids 28, thereby providing accurate control for the production of ozone.

The bridge control circuit 52 comprises an input transistor 56, an isolation transformer 58 and an output transistor 60. The isolation transformer 58 is needed because the bridge network 50 is "floating" at 110 VAC (or 220 VAC). The base of the transistor 56 forms the input 16 for receiving the control signal 48 from the microcontroller 38. The control signal 48 comprises a pulse train generated by the microcontroller 38. According to the invention, either the pulse width or the frequency of the control signal 48 can be varied to control the current flowing through the bridge 50 and the primary winding of the transformer 42. The pulse width (or frequency) of the control signal 48 is selected to produce a target ozone level and the actual amount of ozone being produced is determined through the sensing circuit 44., The collector of the transistor 56 is connected to the primary winding of the isolation transformer 58 so that the pulse train produced by the signal 48 is induced in the secondary winding of the transformer 58. The secondary winding of the transformer 58 is connected to a diode 62 and a capacitor 64. The diode 62 rectifies the output from the secondary winding of the isolation transformer 58 and charges the capacitor 64 to generate a DC voltage. The base of the output transistor 60 is connected to the capacitor 64 through a resistive divider formed from resistors 66,68. Another resistor 70 is connected to the emitter of the transistor 60 to limit the current flowing through the transaistor 60. The values of the resistors are chosen to operate the output transistor 60 in the linear or active region. By operation the output transistor 60 in the active region, a sinusoidal output from the bridge 50 is produced thereby allowing precision linear control of the voltage output from the secondary winding of the transformer 42 which is applied to the grids or electrodes 28.

The sensing circuit 44 is coupled to the secondary winding of the high voltage transformer 42 and provides the microcontroller 38 with data for determining the amount of ozone gas $O_3$ being produced. The microcontroller 38 uses this information to control the operation of the ozone generator 1. The microcontroller 38 can be programmed to respond to commands from another computer (not shown) or the microcontroller 38 can include an input panel (not shown) for manually setting the desired ozone gas level.

FIG. 2 also shows the sensing circuit 44 in more detail. The sensing circuit 44 produces an output signal 72 corresponding to the discharges occurring in the chamber 11 which are also related to the production of ozone gas $O_3$ from the oxygen 24. The microcontroller 38 uses the output 72 from the sensing circuit 44 to calculate the amount of ozone gas $O_3$ being generated by the ozonizer 1. Each time there is a discharge between the electrodes 28 mounted in the chamber 11 (FIG. 1), a pulse is produced in the winding of the high voltage transformer 42. A pickup coil 74 is electromagnetically coupled to the winding of high voltage transformer 42 and pulses due to discharges will induce a current in the pickup coil 74. The sensing circuit 44 detects these pulses and produces the output 72 for the microcontroller 38.

Referring to FIG. 2, the sensing circuit 44 comprises a diode 76, a capacitor 78, a resistor 80 and an operational amplifier 82. The operational amplifier 82 (op amp) is configured as a voltage follower or unity gain buffer and functions as an isolating circuit. The capacitor 78 is charged through the diode 76 by the induced voltage in the pickup coil 74 and provides an input voltage for the op amp 02. The op amp 82 produces a corresponding output pulse 72 which is inputted by the microcontroller 38.

The microcontroller 38 includes program code which determines the amount of ozone $O_3$ produced by the generator 1. The calculation of the concentration of ozone $O_3$ produced is based on three elements: the amount of electrical energy applied to the oxygen 24, the amount of oxygen passing through the chamber 11, and the temperature inside the chamber 11.

The amount of oxygen passing through the chamber is determined from the readings from the flow rate meter 25. The flow rate is measured through the flow meter 25 as the oxygen 24 enters the chamber 11. The controller 38 uses the flow rate to control the flow valve 22 and the flow rate reading is factored into the calculation to determine the concentration of ozone, i.e. milligrams of ozone per litre of oxygen.

For a given energy input rate, the generator 1 produces ozone $O_3$ at a fixed rate, for example x milligrams per minute (assuming the other factors such as temperature are held constant). If the flow rate measured by the meter 25 is y liters of oxygen per minute, then the ozone concentration is determined as x/y milligrams of ozone per liter of oxygen. The amount of electrical energy applied to the oxygen 24 corresponds to the discharge current is measured by the sensing circuit 44 and provided to the microcontroller 38 on output 72. Because the sensing circuit 44 measures the actual discharges in the chamber 11, the output 72 is independent of the high voltage drive 40 and the drive 40 can vary without distorting the output 72 provided the output from the drive 40 does not drop too low.

Preferably the temperature inside the enclosure 11 is also taken into account, because as the temperature inside the enclosure 11 rises the amount of ozone being produced will decrease, and therefore the voltage applied to the grids 28 needs to be increased. In applications where the ozone generator 1 is operated continuously heat is produced and temperature should be taken into account. Humidity is another factor which may be considered if the oxygen 24 is not medical grade and supplied at a regulated pressure.

The microcontroller 38 determines the concentration of the ozone $O_3$ by first determining the amount of ozone being produced, i.e. the base reading, based on the energy input. If the stream of oxygen 24 comprises medical grade oxygen then there is a direct correspondence between the input energy and the amount of ozone $O_3$ generated. The base reading for the ozone $O_3$ is corrected for temperature before calculating the concentration. The base reading of ozone corresponds to the output 72 from the sensing circuit 44. In the preferred embodiment, the microcontroller 38 uses a "look-up" table which contains base values for ozone corresponding to the output 72 readings of the sensing circuit 44. The base reading obtained from the look-up table is then corrected for temperature. The microcontroller 38 has a second look-up table which contains temperature correction factors. The microcontroller 38 scans the temperature sensor 19 and looks up the corresponding temperature correction factor to be applied to the base reading for the ozone. The temperature correction factor table is normalized so that 1.0 is centred at 20° C. The temperature-corrected base reading for ozone is then divided by the flow rate to yield the concentration of ozone $O_3$ in milligrams of ozone per litre for example. If the oxygen 24 does not comprise medical grade oxygen, i.e. pure oxygen, then a further correction factor is introduced into the calculation.

The values for the look-up table are determined empirically, for example by monitoring the output of the generator 1 using a UV based spectrometer (not shown) and the corresponding readings from the output 72 of the sensing circuit 44.

A significant advantage of the sensing circuit 44 and microcontroller 38 arrangement according to the present invention is the capability to perform an ozone measurement "in-line". Because the measurement is taken in-line, the problem of the ozone gas $O_3$ being contaminated or altered by the measurement technique is eliminated.

The microcontroller 38 is implemented using the commercially available PIC16C71 microcontroller available from Microchip Technologies Inc. which has been suitably programmed to perform the processing steps according to the present method. The PIC16C71 controller is a single chip device comprising a microprocessor and "on-chip" program memory, data memory, input/output parts, timers and other on-chip resources.

The control loop is controlling the operation of the ozone generator 1 is preferably implemented as a closed control loop which is realized using a PID (Proportional plus Integral plus Derivative) control mode. A proportional control system operates by first determining the actual value of the quantity to be controlled and the desired value, i.e. set-point, and then applying a correction proportional to this difference. The microcontroller 38 controls the amount of ozone gas $O_3$ being generated by regulating and monitoring the amount of oxygen 24 entering the chamber 11 and/or the voltage applied to the electrode 28. The addition of the integral and derivative terms in the transfer function improved the performance of the control loop. For the ozone control loop, the derivative term is selected to compensate for the sequential lag or the output from electrodes 28 and the generation of zone gas $O_3$ in the chamber 11. The implementation of the control loop in software will be within the understanding of those skilled in the art and further explanation is not needed.

The present invention may be embodied in other specific forms without departing from the spirit or essential characteristics thereof. Therefore, the presently discussed embodiments are considered to be illustrative and not restrictive, the scope of the invention being indicated by the appended claims rather than the foregoing description, and all changes which come within the meaning and range of equivalency of the claims are therefore intended to be embraced therein.

What is claimed is:

1. An apparatus for generating ozone from oxygen provided from an oxygen supply at a known concentration and measurable flow rate, said apparatus comprising:

(a) an enclosure having an inlet for receiving oxygen from said oxygen supply and an outlet for releasing ozone and oxygen;

(b) a plurality of electrodes mounted inside said enclosure and said electrodes being separated by a dielectric;

(c) energizer means for energizing said electrodes, said energizer means having a control input for receiving a control signal and an input port for connecting to a power source;

(d) said energizer means including generator means responsive to said control signal for generating a high voltage at an output coupled to said electrodes for energizing said electrodes and producing an electric field for forming ozone from said oxygen; and (e) means for determining the amount of ozone being produced comprising sensor means coupled to the high voltage output of said generator means for sensing discharge current produced by interaction of said oxygen and said electric field in formation of said ozone, and means for calculating the amount of ozone from the energy in said discharge current and the concentration and flow rate of the oxygen from said oxygen supply.

2. The apparatus as claimed in claim 1, further including a temperature sensor for producing a temperature reading signal indicative of the temperature in said enclosure and said means for calculating being responsive to said temperature reading.

3. The apparatus as claimed in claim 2, wherein said generator means for generating a high voltage output comprises means for producing a controlled AC output responsive to said control signal.

4. The apparatus as claimed in claim 2, wherein said enclosure is formed from medical grade teflon material.

5. The apparatus as claimed in claim 2 or 3, wherein said control signal comprise a pulse width modulated signal.

6. The apparatus as claimed in claim 3, wherein said means for producing a controlled AC output signal responsive to said control signal comprises a transformer having an input port and an output port and a bridge network having an input for connecting to said power source and an output coupled to the input port of said transformer and a bridge control input, and said means for producing a controlled AC output including a switching circuit coupled to the bridge control input for switching said bridge network in response to said control signal to produce said high voltage output at the output port of said transformer.

7. An apparatus for linearly controlling an AC signal for an apparatus for generating ozone, said apparatus comprising:
(a) a bridge network having an input port for receiving an AC signal, and said bridge network including a switching control input and a bridge output port;
(b) a control circuit having an input for receiving a control signal and an output coupled to the switched control input of said bridge network, and said control circuit having means responsive to said control signal for generating a switching control signal at said output for switching said bridge network and producing a controlled power signal at said bridge output port; and
(c) a transformer having an output port and an input port coupled to said bridge output port and means responsive to said controlled power signal for producing a high voltage output signal at said output port.

8. The apparatus as claimed in claim 7, wherein said means for generating a switching control signal comprises a transistor.

9. The apparatus as claimed in claim 7 or 8, wherein said control signal comprises a pulse width modulated signal.

10. The apparatus as claimed in claim 7 or 8, wherein said control signal comprises a square wave having a variable frequency.

11. A sensor for determining the amount of ozone being produced by an ozone generator comprising an enclosure with an inlet for receiving oxygen from an oxygen supply at a known concentration and measurable flow rate and an outlet for releasing ozone and oxygen, and the generator including a plurality of electrodes mounted inside the enclosure and being separated by a dielectric and a high voltage generator having a control input for receiving a control signal, an input port for connecting to a power source and an output coupled to the electrodes for energizing the electrodes in response to the control signal and producing an electric field for forming ozone from the oxygen, said sensor comprising:
(a) sensing means coupled to the output of the high voltage generator for sensing a discharge current produced by the interaction of the oxygen with the electrical field in the formation of ozone;
(b) means for determining the amount of ozone being produced by the ozone generator from said discharge current;
(c) said means for determining the amount of ozone being responsive to the concentration and flow rate of the oxygen being supplied by the oxygen supply.

12. The sensor as claimed in claim 11, wherein said sensing means comprises a coil electromagnetically coupled to the output of the high voltage generator.

13. The sensor as claimed in claim 12, wherein said means for determining the amount of ozone being produced comprises a programmed microcontroller coupled to receive a signal corresponding to said discharge current and data corresponding to the concentration and flow rate of the oxygen.

14. The sensor as claimed in claim 13, wherein said sensing means includes an amplifier coupled to the output of said coil and having means for generating said signal for said microcontroller.

15. The sensor as claimed in claim 14, wherein said ozone generator further includes a temperature sensor for producing a temperature reading signal indicative of the temperature in said enclosure and said microcontroller having an input for receiving said temperature reading signal.

16. The sensor as claimed in claim 15, wherein said ozone generator further includes a flow rate meter coupled to the oxygen supply and having means for generating a flow rate reading for said microcontroller.

17. The sensor as claimed in claim 16, wherein said control signal comprises a pulse width modulated signal.

18. A sensor for determining the amount of ozone being produced by an ozone generator comprising an enclosure with an inlet for receiving oxygen from an oxygen supply at a known concentration and measurable flow rate and an outlet for releasing ozone and oxygen, and the generator including a plurality of electrodes mounted inside the enclosure and being separated by a dielectric and a high voltage generator having a control input for receiving a control signal, an input port for connecting to a power source and an output coupled to the electrodes for energizing the electrodes in response to the control signal and producing an electric field for forming ozone from the oxygen, said sensor comprising:
(a) sensing means coupled to the output of the high voltage generator for sensing a discharge current produced by the interaction of the oxygen with the electric field in the formation of ozone, said sensing means comprising a coil electromagnetically coupled to the output of the high voltage generator and an amplifier coupled to the output of said coil for generating a signal corresponding to said discharge current; and
(b) a microcontroller coupled to receive said signal and having means for reading the concentration and flow rate levels of the oxygen being supplied by the oxygen supply and means for determining the amount ozone being produced by the ozone generator.

19. An apparatus for generating ozone from an oxygen supply, said apparatus comprising:
(a) an enclosure having an inlet for receiving said oxygen supply and an outlet for releasing ozone and oxygen;
(b) a plurality of electrodes mounted inside said enclosure and said electrodes being separated by a dielectric;
(c) energizer means for energizing said electrodes, said energizer means having a control input for receiving a control signal and an input port for connecting to a power source;
(d) said energizer means including generator means for generating a controllable AC voltage at an output in response to said control signal, and said output being coupled to said electrodes for energizing and producing an electric field for forming ozone from said oxygen; and (e) said generator means for generating a controllable AC voltage including a transformer having an input port and an output port and a bridge network having an input for connecting to said power source and an output coupled to the input port of said transformer and a bridge control input, and said generator means including a switching circuit coupled to the bridge control input for switching said bridge network in response to said control signal to produce said high voltage output at the output port of said transformer.

* * * * *